United States Patent [19]

Cohen

[11] Patent Number: 5,690,672
[45] Date of Patent: Nov. 25, 1997

[54] TOURNIQUET APPARATUS WITH REPLACEABLE COVER

[75] Inventor: Robert A. Cohen, Atlanta, Ga.

[73] Assignee: Dignity Wear, Ltd., Boca Raton, Fla.

[21] Appl. No.: 662,038

[22] Filed: Jun. 12, 1996

[51] Int. Cl.⁶ .................................................. A61B 17/00
[52] U.S. Cl. ................................................... 606/203
[58] Field of Search ........................... 606/203, 202, 606/201, 204; 128/677

[56] References Cited

U.S. PATENT DOCUMENTS

| | | |
|---|---|---|
| 1,366,121 | 1/1921 | Dorsey . |
| 3,654,931 | 4/1972 | Hazlewood .................... 128/327 |
| 4,406,281 | 9/1983 | Hubbard et al. ................. 128/132 |
| 4,878,274 | 11/1989 | Patricy ............................ 606/203 |
| 5,234,459 | 8/1993 | Lee .................................. 606/203 |

*Primary Examiner*—Michael Buiz
*Assistant Examiner*—Kevin Truong
*Attorney, Agent, or Firm*—Kennedy, Davis & Kennedy

[57] ABSTRACT

A tourniquet apparatus (10) has an elongated, distensible tourniquet member (12), and a disposable tourniquet cover (40) comprised of an outer liquid-permeable layer (60), an inner absorbent padded layer (70), and a liquid-impermeable layer (80). Adhesive strips (51) and (53) on the tourniquet cover back side (42) peripheral side edges (46) and (48) allow the cover to be easily positioned and removed from the tourniquet (12). Blood or other bodily fluids are trapped in the padded layer without soiling the tourniquet (12). Cover (40) can also be used to protect reusable blood pressure cuffs from soiling.

5 Claims, 2 Drawing Sheets

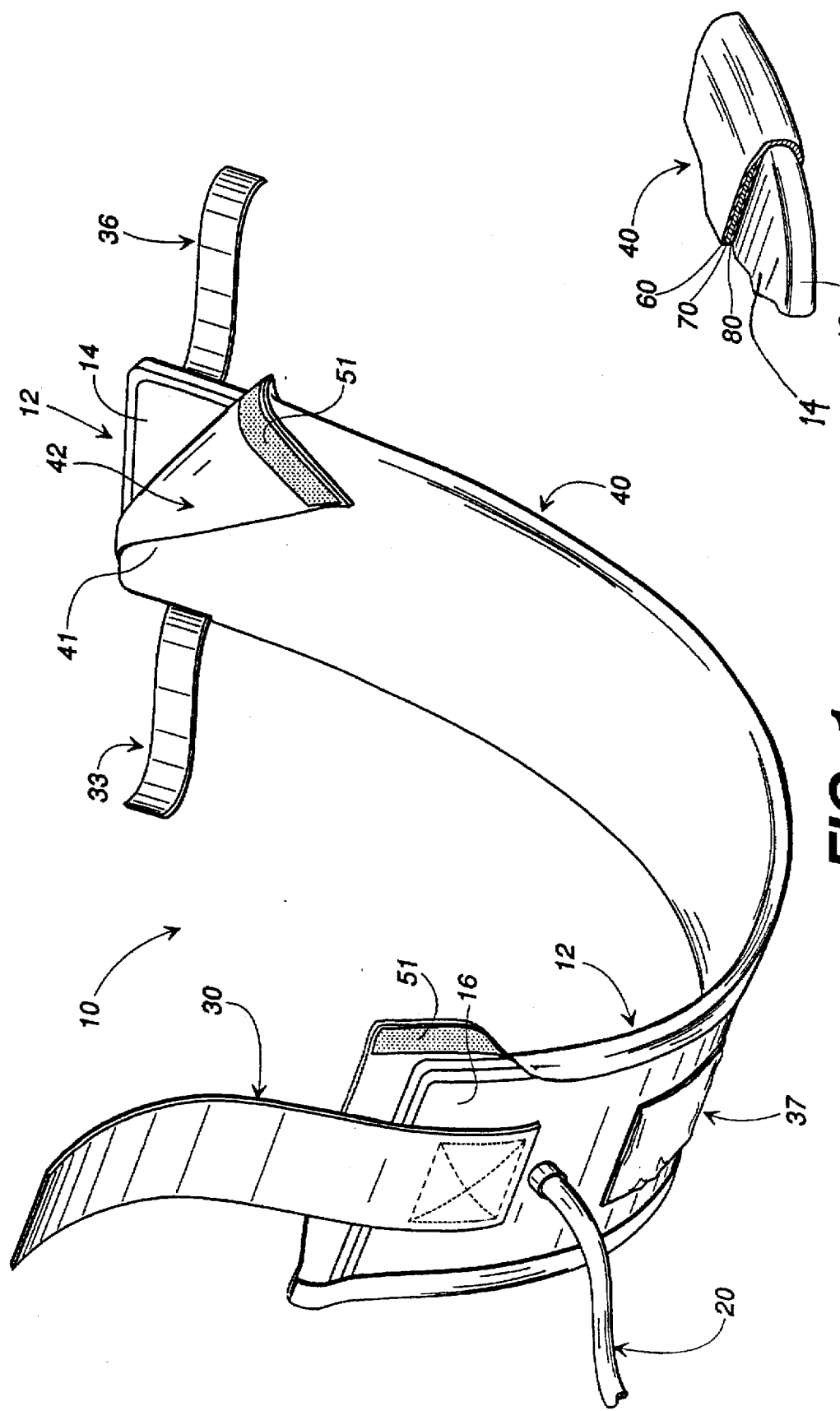

TOURNIQUET APPARATUS WITH REPLACEABLE COVER

TECHNICAL FIELD

This invention relates generally to tourniquets and other devices such as blood pressure cuffs that are strapped about body extremities.

BACKGROUND OF THE INVENTION

In hospital environments and emergency medical situations it is sometimes necessary to apply a tourniquet (sometimes called a tourniquet cuff) around a body limb to control the flow of blood. Tourniquets today typically are made of a flexible, elongated, distensible bladder. The tourniquet is wrapped around a patient's limb and then is distended in order to exert pressure on the limb. In this regard, a tourniquet typically is inflated with air.

Tourniquets are commonly used in hospital operating rooms and in emergency medical services offered by ambulance staff. In use, tourniquets frequently are exposed to bodily fluids, such as blood and perspiration, and to topical ointments, medications, and sterilants. Under current medical protocols, soiled tourniquets cannot be reused on other patients unless cleaned sufficiently. This lack of ready reusability has made the cost of existing tourniquets quite high.

Some companies, such as InstruMed, Inc. of Bothell, Wash., offer disposable tourniquets for use in reducing the risk of cross-contamination between patients (after one use, the entire tourniquet is disposed of). While it is more efficient time-wise to use disposable tourniquets than to clean tourniquets, the costs of these disposable tourniquets is still high. In this regard, hospital staffs have been prompted to develop various covers for operating room tourniquets in order to protect the tourniquets from blood and other fluids. In some instances, materials from the operating rooms themselves have been used by hospital personnel to protect the tourniquets from contamination. Many of these materials (e.g., fabrics and linens) are porous and allow for the eventual transmission of fluid through the material to the tourniquet. Additionally, the use of these supplemental materials (the covers) can lead to uneven pressure on the patient's skin and in some instances discomfort.

U.S. Pat. No. 1,366,121 describes a bandage made of a fabric that is connected to an inflatable bag. A pocket is formed in one end of the bandage for receiving the inflatable bag therein. The bag can be removed so that the fabric of the bandage can be sterilized. However, the bodily fluids are passed through the bag to the tourniquet, thereby exposing the tourniquet to contamination.

U.S. Pat. No. 3,654,931 describes a disposable cover for an inflatable tourniquet with a tongue/fastening strap. The cover includes a plastic envelope for receiving and covering the inflatable tourniquet and a plastic sheet extending from one end of the envelope for covering the tongue/fastening strap.

U.S. Pat. No. 4,406,281 discloses a fluid-impermeable cover for use with operating room tourniquets. The cover is comprised of a thin sheet of a flexible, liquid-impermeable material that has a length sufficient to be wrapped around a limb of a patient. A separate pad is positioned on one side of the sheet to provide cushioning. A fastener is attached to one edge of the sheet so that as the sheet is wrapped around the patient's limb, it can be held in place by the fastener so that the tourniquet can be placed over the cover. The sheet has a width which is wider than the tourniquet so that after the tourniquet is applied to the patient's limb, the sheet can then be folded over the tourniquet to shield it from moisture and contamination, such as from blood or ointments.

Blood pressure cuffs are typically used by hospital emergency rooms and emergency medical services to take a patient's vital signs. A situation commanding emergency medical care often entails exposure of this medical instrument to bodily fluids. Current medical protocol often requires that before a medical instrument can be reused on other patients, that it be cleaned using alcohol swabs or Betadine® to prevent cross-contamination between patients. Often, the short time period between patient cases which require use of a tourniquet or blood pressure cuff precludes extensive cleaning procedures for these instruments. In an effort to meet with medical protocol and provide rapid response in emergency situations, disposable blood pressure cuffs have been developed for use with the automated blood pressure monitors typically used in emergency rooms. The disposable cuffs are cumbersome to attach to blood pressure monitors, and are themselves fairly expensive. An example of such a cuff is manufactured by Ethicon, a division of Johnson & Johnson.

Despite these developments in the prior art, there remains yet a need for tourniquet and blood pressure cuff apparatuses which have a lower cost and which avoid cross-contamination from one patient to the next. It is to the provision of such apparatus that the present invention is primarily directed.

SUMMARY OF THE INVENTION

Briefly described, in one preferred form of the present invention, a tourniquet apparatus includes a reusable, elongated, distensible member with side edges and end edges. The distensible member is adapted to be wrapped about and secured about a body extremity for applying pressure to the body extremity. The apparatus further comprises a replaceable cover for preventing body fluids and topical dressings from contacting and contaminating the distensible member. The cover has a liquid-permeable layer, a liquid-impermeable layer, and an inner absorbent pad positioned between the liquid-permeable layer and the liquid-impermeable layer. The liquid-impermeable layer is sized to be wrapped about the side edges of the distensible member and has means for releasably securing the cover to the distensible member. This apparatus prevents fluids from contacting the distensible member, which fluids would otherwise contact the distensible member.

In another preferred form of the invention, a replaceable cover for use with a distensible medical apparatus member having side and end edges, such as a tourniquet or blood pressure cuff, for preventing body fluids and topical dressings from contacting and contaminating the distensible medical apparatus member comprises a liquid-permeable layer, a liquid-impermeable layer, and an inner absorbent pad positioned between the liquid-permeable layer and the liquid-impermeable layer. The liquid-impermeable layer is sized to be wrapped about the side edges of the distensible member. Means are provided for releasably securing the cover to the distensible member.

The invention has numerous advantages. For example, the apparatus including the cover can be applied easily to the patient's extremities, and are comfortable for the patient. The cover helps to maintain the distensible member (for example, the tourniquet or blood pressure cuff) in a sanitary condition. The cover can be quickly and easily removed from the tourniquet member or blood pressure cuff after use. Additionally, the cover can be easily and inexpensively manufactured. Furthermore, this invention provides for a very cost-effective solution, as compared with known apparatus. The invention is highly effective at avoiding or preventing cross-contamination between patients, while allowing medical personnel to quickly comply with medical protocol in emergency situations.

Accordingly, it is a primary object of the present invention to provide a tourniquet apparatus with a replaceable cover which is inexpensive and yet protects against cross-contamination.

It is another object of the present invention to provide a tourniquet apparatus or blood pressure cuff apparatus with a replaceable cover which can be applied and removed easily and quickly.

It is another object of the present invention to provide a removable cover for use with tourniquets and blood pressure cuffs which can be manufactured inexpensively.

These and other objects, features, and advantages of the present invention will become apparent upon reading the following specification in conjunction with the accompanying drawing figures.

BRIEF DESCRIPTION OF THE DRAWINGS

FIG. 1 is a perspective illustration of a tourniquet with a replaceable cover that embodies principles of the invention in a preferred form.

FIG. 1A is a cross-sectional, perspective illustration of a portion of the apparatus of FIG. 1.

FIG. 2A is an exploded, perspective view of the replaceable tourniquet cover of FIG. 1 while

DETAILED DESCRIPTION OF THE PREFERRED EMBODIMENTS

Figure 2A:
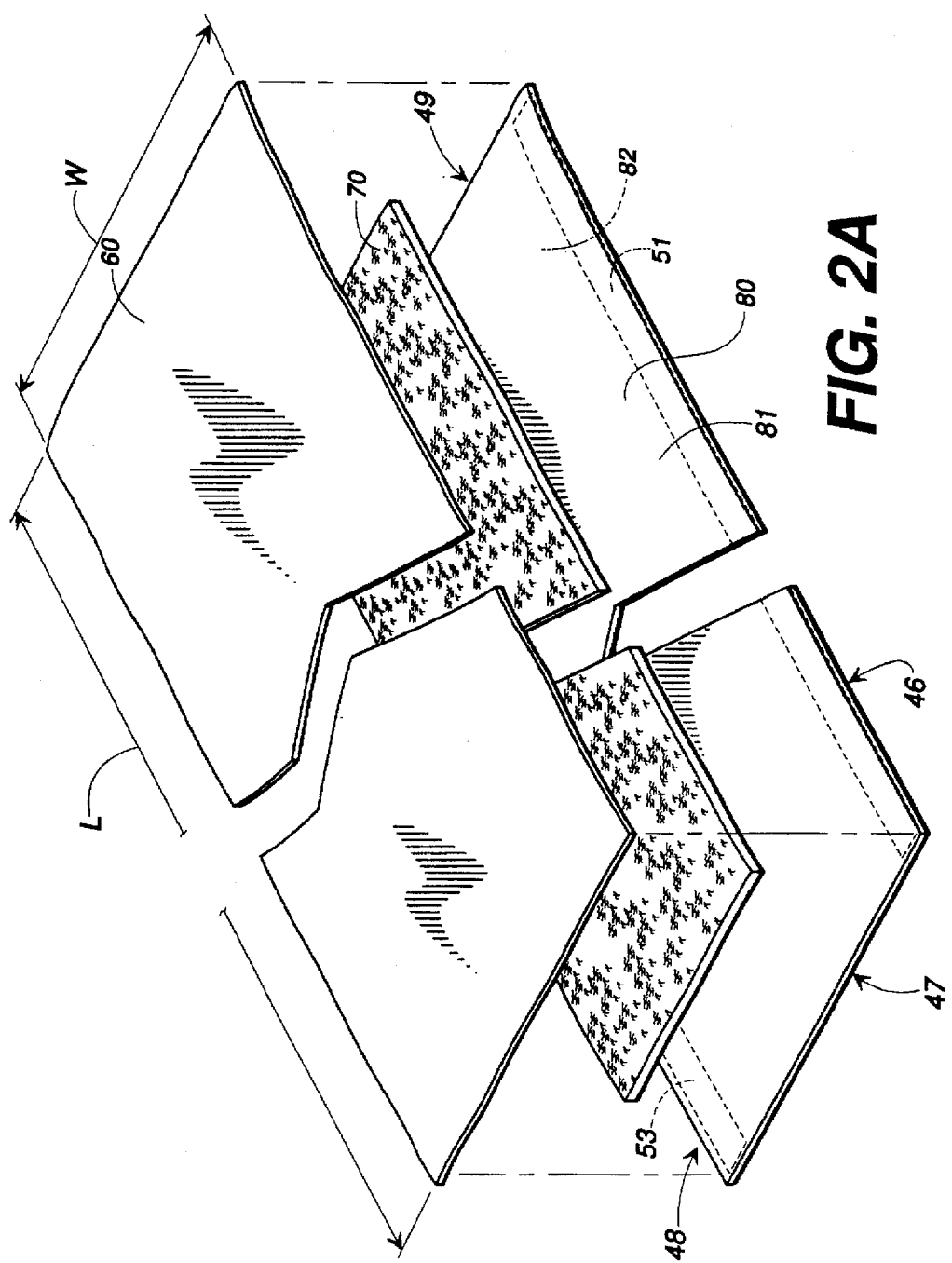

Referring now in detail to the drawing figures, wherein like reference numerals represent like parts throughout the several views, FIG. 1 shows a tourniquet apparatus 10 according to a preferred form of the invention. The tourniquet apparatus 10 includes an elongated, distensible tourniquet member 12 having a back side 14 and a front side 16. The tourniquet member 12 is conventional, such as that available from InstruMed, Inc. of Bothell, Washington, or from Smith & Nephew Richards Inc. of Ireland. Tourniquet member 12 has an air hose 20 and attached fastening straps 30, 33, and 36. A fastening means such as a strip of Velcro® (hook and loop fastening elements) 37 is placed along the front side 16 of the tourniquet member 12 to help maintain the tourniquet in position after it has been wrapped around a limb.

A disposable tourniquet cover 40 having a front side 41 and a back side 42 is initially positioned with its back side 42 over the back side 14 of the tourniquet. Tourniquet cover 40 has a width W and length L greater than the corresponding width and length of the underlying tourniquet member 12 (see FIG. 2A). Preferably, as seen in FIG. 1 and in FIG. 2A, edges 46, 47, 48, and 49 with adhesive strips 51 and 53 along the back side 42 peripheral side edges 46 and 48, extend beyond the width and length of the tourniquet member 12 so that they can be folded over the tourniquet side edges when the cover is applied. Preferably, the adhesive strips are placed on the back side 42 of the tourniquet cover 40 along the cover peripheral side edges and are themselves covered with strip covers 55 (see FIG. 2B) to maintain the tackiness of the strips while not in use. Alternatively, other fastening means such as tape can be placed on the cover to secure the cover to the tourniquet member.

Figure 2B:
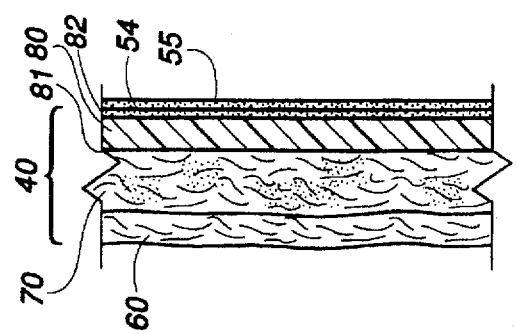
FIG. 2B is a cross-sectional view thereof.

As shown in FIGS. 1A, 2A, and 2B, tourniquet cover 40 preferably is comprised of a trilaminate comprising an outer liquid-permeable layer 60, an intermediate padded, absorbent layer 70, and an inner liquid-impermeable layer 80. Liquid-permeable layer 60 allows for the passing of bodily fluids or oils and topical medications through to pad 70 where the fluid is held in place. Liquid-permeable layer 60 and intermediate padded absorbent layer 70 preferably are non-woven. Liquid-impermeable layer 80 prevents the fluid held in absorbent layer 70 from passing through to tourniquet back side 14.

Liquid-permeable layer 60 preferably is held to inner liquid-impermeable layer 80 along its perimeter by thermal bonding, but can be held by adhesive or stitching as well. Liquid-permeable layer 60 and liquid-impermeable layer 80 preferably are the same size and shape, preferably rectangular, each having straight edges 46, 47, 48, and 49. Intermediate padded layer 70 preferably is rectangular in shape having a width and length smaller that than that of layers 60 and 80. Absorbent padded layer 70 is held within the envelope of inner and outer layers 60 and 80. Liquid-impermeable layer 80 has upper and lower surfaces 81 and 82, respectively. Adhesive strips 51 and 53 (54 generally in FIG. 2B) are positioned on the lower surface 82 of inner layer 80 along each of the peripheral side edges 46 and 48. The adhesive strips can be provided with removable covers 55 so that the adhesive remains viable during storage. Additional adhesive strips optionally can be positioned on the lower surface 82 of inner layer along peripheral end edges 47 and 49.

In the preferred embodiment, the liquid-permeable layer 60 is a fabric made of polypropylene fibers, derived from polypropylene resin, which fibers are bonded together by heat and calendared to produce a thin web-like material. The liquid-permeable layer basis weight preferably is no less than 16 grams per square meter and no greater than 50 grams per square meter.

The inner absorbent pad 70 preferably is a cellulose and super absorbent polymer composite airlaid nonwoven pad. The composite pad having high retention and fast absorption, is constructed by "airlaying" cellulose fibers and super absorbent polymer into a web and bonding these materials to produce a sheet that will act as the absorbent core. Super-absorbent polymer is derived from glacial acrylic acid. The basis weight of this pad preferably is 450 grams per square meter and preferably it is made of approximately 80% cellulose fiber and 20% super-absorbent powder. The pad preferably has a thickness of between 2.67 and 3.37 mm/ply.

The liquid-impermeable layer 80 preferably is a polyethylene film. This layer is a plastic film constructed from polyethylene resin. The basis weight of the film preferably is about 25 to 50 grams per square meter.

The adhesive strips preferably are double-sided tape, constructed of hot-melt adhesive. For the purposes of this application, Hot-melt adhesive is defined as a "non-volatile solid thermoplastic adhesive which is applied in a molten state and which sets and forms a bond to a substrate or substrates upon cooling". Hot-melt contains a polymer based on latex, a tackifier, a diluent (an oil or wax), and an antioxidant (for degradation prevention). It is applied to a silicone coated release paper to create "tape". This tape is applied to the polyethylene film and acts as an anchor for the device when used.

To prepare the tourniquet apparatus 10 for use, tourniquet cover 40 is positioned over tourniquet back side 14 so that the side edges (46, 48) of the cover hang over the sides of tourniquet member 12. The cover side edges 46 and 48 are then folded around the sides of tourniquet member 12 and then adhered in place onto tourniquet front side 16 using the adhesive strips 51 and 53. If the adhesive strips are covered for storage purposes, the adhesive strip covers 55 are first removed before the cover edges are wrapped around the sides of tourniquet member 12.

To use the prepared tourniquet apparatus for a surgical procedure, the tourniquet apparatus is wrapped around the limb of a patient and pressure (such as from ambient air) is applied to distend the tourniquet so that the flow of blood past the tourniquet apparatus is either reduced or eliminated. As blood flows from a wound near tourniquet member 12, or ointments or medications rub from the skin of the patient, the fluid passes through liquid-permeable layer 60 into absorbent pad 70. Liquid-impermeable layer 80 thus prevents the contamination of tourniquet member 12 by trapping the fluid in absorbent pad 70 and preventing it from coming into contact with the tourniquet back side surface 14. Upon completion of the surgical 10 procedure, the tourniquet is removed from the patient and the tourniquet cover 40 is peeled off of tourniquet member 12 and the cover alone is disposed of. Tourniquet member 12 can then be cleaned (if necessary) and refitted with a new cover with minimal effort, thereby quickly, effectively, and cheaply restoring the tourniquet apparatus 10 for new use. The cost of tourniquet covers 40 is minimal in comparison to the cost associated with cleaning reusable tourniquets or in comparison to single-use disposable tourniquets.

Thus, it can be seen that the tourniquet apparatus with replaceable cover according to the present invention can be applied to a patient's limb easily without the likelihood of material gathering under the tourniquet apparatus 10 resulting in added discomfort to a patient. The tourniquet member 12 remains sanitary and can be reused, while the soiled replaceable cover 40 can be removed and disposed of quickly and easily.

The disposable tourniquet cover 40 can also be used on non-disposable blood pressure cuffs to ensure sanitary hospital conditions and to prolong the life of the cuff without significant affect on a blood pressure reading.

To prepare a blood pressure cuff apparatus for use, a replaceable cover 40 is positioned over a distensible blood pressure cuff, in particular, over the side to face a patient's limb. The side edges of cover 40 are then folded around the sides of the distensible blood pressure cuff and then adhered in place onto the cuff using adhesive strips 51 and 53. To use the prepared blood pressure cuff apparatus, the blood pressure cuff apparatus is wrapped around the limb of a patient and air pressure is applied so that the blood pressure of the patient can be monitored on a corresponding meter. Any liquid substance which is on the patient's skin under the cuff passes through liquid-permeable layer 60 and into absorbent pad 70.

Liquid-impermeable layer 80 thus prevents the contamination of the blood pressure cuff by trapping the fluid in absorbent pad 70 and preventing it from coming into contact with the cuff itself. Upon completion of the blood pressure reading, the apparatus is removed from the patient and the replaceable cover 40 is peeled off of the cuff and disposed of. The blood pressure cuff can then be cleaned (if necessary) and refitted with a new cover with minimal effort, effectively and cheaply restoring the blood pressure cuff for new use.

It thus is seen that an apparatus is now provided which gives patient comfort, while providing a barrier layer to prevent the soiling of a tourniquet or a blood pressure cuff during a medical procedure. The reusable tourniquet apparatus and blood pressure cuff apparatus allows for the absorption of bodily fluids with reduced risk of cross-contamination from contact with bodily fluids.

While the invention has been described in detail with particular reference to a preferred embodiment thereof, it should be understood that many modifications, additions, and deletions can be made thereto without departure from the spirit and scope of the invention as set forth in the following claims.

I claim:

1. A tourniquet apparatus comprising:

a reusable, elongated, distensible member adapted to be wrapped about and secured about a body member for applying pressure to the body member, said elongated, distensible member having side edges;

a replaceable cover for preventing body fluids and topical dressings from contacting and contaminating said elongated, distensible member, said cover having a liquid-impermeable layer, a liquid-permeable layer, and an inner absorbent pad between said liquid-permeable layer and said liquid-impermeable layer, and wherein said liquid-impermeable layer is sized to be wrapped about said side edges of said elongated, distensible member; and a means for releasably securing said cover to said elongated, distensible member, whereby fluids that otherwise would normally come into contact with the elongated, distensible member pass through the liquid-permeable layer to the inner absorbent pad where they are prevented from contacting the elongated, distensible member by the liquid-impermeable layer.

2. The tourniquet apparatus of claim 1 wherein said cover further includes fastening means on said liquid-impermeable layer for fastening said cover to said elongated, distensible member.

3. The tourniquet apparatus of claim 2 wherein said fastening means comprises an adhesive strip.

4. The tourniquet apparatus of claim 1 wherein said liquid-permeable layer comprises a non-woven material.

5. The tourniquet apparatus of claim 1 wherein said inner absorbent pad comprises a non-woven material.

* * * * *